United States Patent [19]

Kraatz et al.

[11] Patent Number: 4,631,288
[45] Date of Patent: Dec. 23, 1986

[54] TRIAZOLYLMETHYL-PYRIDYLOXYMETHYL-CARBINOL FUNGICIDES

[75] Inventors: Udo Kraatz, Leverkusen; Karl H. Büchel, Burscheid; Gerd Hänssler, Leverkusen; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 651,002

[22] Filed: Sep. 14, 1984

[30] Foreign Application Priority Data

Sep. 23, 1983 [DE] Fed. Rep. of Germany ....... 3334409

[51] Int. Cl.$^4$ .................... C07D 401/12; A61K 31/41
[52] U.S. Cl. ..................................... 514/340; 514/188; 514/191; 546/276; 546/2
[58] Field of Search .................... 546/276, 2; 514/188, 514/191, 340

[56] References Cited

FOREIGN PATENT DOCUMENTS

| | | |
|---|---|---|
| 0045016 | 2/1982 | European Pat. Off. . |
| 0047594 | 3/1982 | European Pat. Off. . |
| 0061835 | 10/1982 | European Pat. Off. . |
| 0091309 | 10/1983 | European Pat. Off. ............ 548/262 |
| 3018866 | 5/1980 | Fed. Rep. of Germany . |
| 2908378 | 9/1980 | Fed. Rep. of Germany . |
| 2921168 | 12/1980 | Fed. Rep. of Germany . |
| 3000244 | 7/1981 | Fed. Rep. of Germany . |

*Primary Examiner*—Jane T. Fan
*Attorney, Agent, or Firm*—Sprung Horn Kramer & Woods

[57] ABSTRACT

Novel triazolylmethyl-pyridyloxymethyl-carbinols of the formula

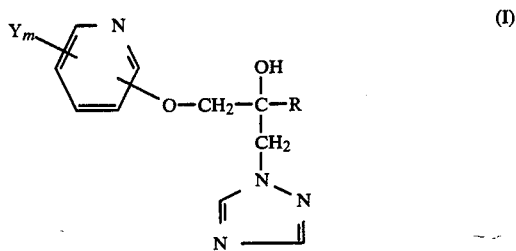

(I)

in which
R is optionally substituted alkyl, optionally substituted cycloalkyl or optionally substituted phenyl,
Y is halogen, alkyl, alkoxy or cyano, and
m is 0, 1, 2, 3 or 4, or addition products thereof with acids or metal salts, which possess fungicidal activity.

9 Claims, No Drawings

TRIAZOLYLMETHYL-PYRIDYLOXYMETHYL-CARBINOL FUNGICIDES

The present invention relates to new triazolylmethyl-pyridyloxymethyl-carbinol derivatives, a process for their preparation and their use as fungicides.

It has already been disclosed that certain 3,3-dimethyl-1-phenoxy-2-(1,2,4-triazol-1-yl-methyl)-2-butanols or 1-phenoxy-2-phenyl-3-(1,2,4-triazol-1-yl)-2-propanols which are substituted in the phenyl part have good fungicidal properties (application Ser. No. 549,867, filed Nov. 8, 1983, now pending, corresponding to German Published Specification DE-OS No. 3,018,866). However, the action of these compounds is not always completely satisfactory, especially when low amounts and concentrations are applied.

New triazolylmethyl-pyridyloxymethyl-carbinol derivatives of the general formula (1)

$$Y_m \underset{}{\overset{}{\bigotimes}} - O - CH_2 - \underset{\underset{\underset{N \diagdown_{N}}{\overset{|}{\underset{N}{\diagup}}}}{\overset{|}{\underset{CH_2}{\overset{|}{C}}}}}{\overset{OH}{\overset{|}{C}}} - R \qquad (I)$$

in which

R represents optionally substituted alkyl, optionally substituted cycloalkyl or optionally substituted phenyl;

Y represents halogen, alkyl, alkoxy or cyano and m represents the number 0, 1, 2, 3 or 4, and acid addition salts and metal salt complexes thereof, have now been found.

The compounds of the formula (I) have an asymmetric carbon atom and can therefore be obtained in the two optical isomer forms.

It has furthermore been found that the triazolylmethyl-pyridyloxymethyl-carbinol derivatives of the formula (I) are obtained when oxiranes of the formula (II)

$$Y_m \underset{}{\overset{}{\bigotimes}} - O - CH_2 - \underset{O \diagup \diagdown CH_2}{\overset{}{C}} - R \qquad (II)$$

in which

R, Y and m have the abovementioned meaning, are reacted with 1,2,4-triazole of the formula (III)

$$M - N \underset{\diagdown = N}{\overset{N \diagup =}{\diagup}} \qquad (III)$$

in which

M represents hydrogen or an alkali metal, in the presence of a diluent and if appropriate in the presence of a base, and, if appropriate, an acid or a metal salt is then added on.

It has also been found that the new triazolylmethyl-pyridyloxymethyl-carbinol derivatives of the formula (I) have powerful fungicidal properties.

Surprisingly, the triazolylmethyl-pyridyloxymethyl-carbinol derivatives of the formula (I) according to the invention display better fungicidal actions than the abovementioned 3,3-dimethyl-1-phenoxy-2-(1,2,4-triazol-1-yl-methyl)-2-butanols and 1-phenoxy-3-phenyl-3-(1,2,4-- triazol-1-yl)-2-propanols which are known from the prior art and are closely related compounds structurally and from the point of view of their action. The active compounds according to the invention thus represent an enrichment of the art.

Formula (I) provides a general definition of the triazolylmethyl-pyridyloxymethyl-carbinol derivatives according to the invention. In this formula, preferably, R represents straight-chain or branched alkyl with 1 to 4 carbon atoms, or represents cycloalkyl which has 3 to 7 carbon atoms and is optionally monosubstituted or polysubstituted by identical or different substituents, substituents which may be mentioned being: halogen, alkyl with 1 to 4 carbon atoms and alkoxy with 1 or 2 carbon atoms, or represents phenyl which is optionally monosubstituted or polysubstituted by identical or different substituents, possible substituents being the substituents on phenyl mentioned below for $R^3$, or represents the grouping, $$\underset{CH_2R^2}{\overset{CH_2R^1}{\overset{|}{\underset{|}{-C-CH_3}}}} \quad \text{or} \quad \underset{CH_3}{\overset{CH_3}{\overset{|}{\underset{|}{-C-(CH_2)_n-R^3}}}}$$

wherein $R^1$ represents hydrogen or halogen;

$R^2$ represents halogen and $R^3$ represents alkyl, alkoxy or alkylthio with in each case 1 to 4 carbon atoms, or represents halogenoalkoxy or halogenoalkylthio with in each case 1 or 2 carbon atoms and 1 to 5 identical or different halogen atoms, such as fluorine and chlorine atoms, or represents alkenyl with 2 to 6 carbon atoms, alkoxycarbonyl with 1 to 4 carbon atoms in the alkyl part or cyano, or represents phenyl, phenoxy, phenylthio, phenylalkoxy with 1 to 4 carbon atoms in the alkyl part or phenyl-alkylthio with 1 to 4 carbon atoms in the alkyl part, each of which is optionally monosubstituted or polysubstituted, preferred substituents on the phenyl which may be mentioned in each case being: halogen, alkyl with 1 to 4 carbon atoms, alkoxy and alkylthio with in each case 1 or 2 carbon atoms, halogenoalkyl, halogenoalkoxy and halogenoalkylthio with in each case 1 or 2 carbon atoms and 1 to 5 identical or different halogen atoms, such as, in particular, fluorine and chlorine atoms, cyclohexyl, dialkylamino with 1 to 4 carbon atoms in each alkyl part, nitro, cyano, alkoxycarbonyl with 1 to 4 carbon atoms in the alkyl part and phenyl which is optionally substituted by halogen, and n represents the number 0, 1 or 2;

Y represents halogen, straight-chain or branched alkyl and/or alkoxy with in each case 1 to 4 carbon atoms or cyano and m represents the number 0, 1, 2, 3 or 4.

Particularly preferred compounds of the formula (I) are those in which

R represents tert.-butyl or isopropyl, or represents cyclopropyl, cyclopentyl or cyclohexyl, each of which is optionally mono-, di- or tri-substituted by identical or different substituents, substituents which may be mentioned in each case being: methyl, ethyl, isopropyl, methoxy and ethoxy, or represents phenyl which is optionally mono-, di- or tri-substituted by identical or different substituents, substituents which may be mentioned being: fluorine, chlorine, methyl, trifluoromethyl, phenyl and chlorophenyl, or represents the grouping

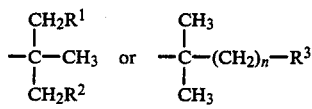

wherein $R^1$ represents hydrogen, fluorine or chlorine;

$R^2$ represents fluorine or chlorine;

$R^3$ represents methyl, ethyl, propyl, methoxy, ethoxy, methylthio, ethylthio, trifluoromethoxy, trifluoromethylthio, vinyl, methoxycarbonyl, ethoxycarbonyl or cyano, or represents phenyl, phenoxy, phenylthio, phenylmethoxy or phenylmethylthio, each of which is optionally substituted, substituents on the phenyl which may be mentioned in each case being: fluorine, chlorine, methyl, ethyl, methoxy, methylthio, trifluoromethyl, trifluoromethoxy, trifluoromethylthio, dimethylamino, methoxycarbonyl and ethoxycarbonyl, and n represents the number 0, 1 or 2;

Y represents fluorine, chlorine, bromine, iodine, methyl, ethyl, methoxy or cyano and m represents the number 0, 1, 2, 3 or 4.

Very particularly preferred compounds of the formula (I) are those in which

R represents tert.-butyl, or represents phenyl which is optionally mono-, di- or tri-substituted by identical or different substituents, substituents which may be mentioned being: fluorine, chlorine, methyl, trifluoromethyl, phenyl and chlorophenyl, or represents the grouping

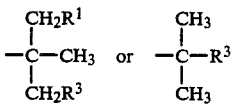

wherein $R^1$ represents hydrogen, fluorine or chlorine, $R^2$ represents fluorine or chlorine and $R^3$ represents phenoxy, phenylthio, phenylmethoxy or phenylmethylthio, each of which is optionally mono- or di-substituted by identical or different substituents, substituents on the phenyl which may be mentioned in each case being: fluorine, chlorine, methyl, methoxy, methylthio, trifluoromethyl, trifluoromethoxy, trifluoromethylthio, methoxycarbonyl and ethoxycarbonyl;

Y represents fluorine, chlorine, bromine or iodine and m represents the number 0, 1, 2 or 3.

Addition products of acids and those triazolylmethyl-pyridyloxymethyl-carbinol derivatives of the formula (I) in which the substituents R and $Y_m$ have the meanings which have already been mentioned as preferred for these substituents are also preferred compounds according to the invention.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Addition products of salts of metals of main groups II to IV and of sub-groups I and II and IV to VIII and those triazolylmethyl-pyridyloxymethyl-carbinol derivatives of the formula (I) in which the substituents R and $Y_m$ have the meanings which have already been mentioned as preferred for these substituents are also preferred compounds according to the invention.

Salts of copper, zinc, manganese, magnesium, tin, iron and nickel are particularly preferred here. Possible anions of these salts are those which are derived from those acids which lead to physiologically acceptable addition products. In this connection, particularly preferred acids of this type are the hydrogen halide acids, such as, for example, hydrochloric acid and hydrobromic acid, and furthermore phosphoric acid, nitric acid and sulphuric acid.

If, for example, 2-[2-(4-chlorobenzyloxy)-prop-2-yl]-2-(6-chloropyridin-2-yloxymethyl)-oxirane and 1,2,4-triazole are used as starting substances, the course of the process according to the invention can be represented by the following equation:

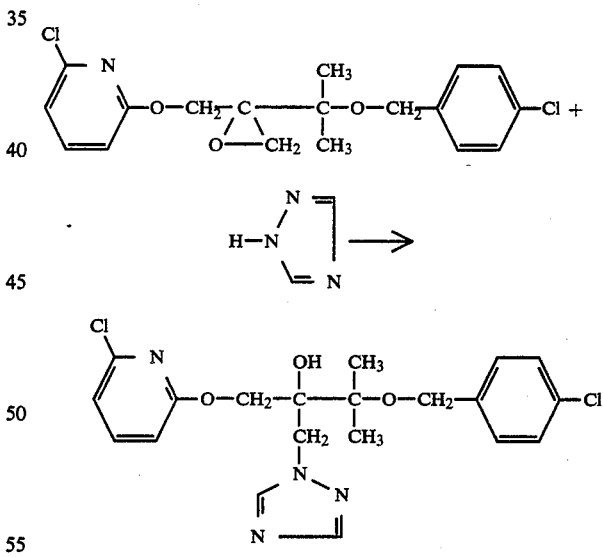

Formula (II) provides a general definition of the oxiranes to be used as starting substances in carrying out the process according to the invention. In this formula, R, Y and the index m preferably have the meanings which have already been mentioned as preferred for these substituents or for the index m in connection with the description of the substances of the formula (I) according to the invention.

The oxiranes of the formula (II) are not yet known. They are useful intermediates and can be obtained in a generally known manner, by reacting ketones of the formula (IV)

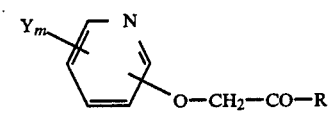

in which

R, Y and m have the abovementioned meaning, either (α) with dimethyloxosulphonium methylide of the formula (V)

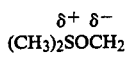

in the presence of a diluent, or (β) with trimethylsulphonium methyl-sulphate of the formula (VI)v

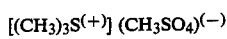

in the presence of an inert organic solvent and in the presence of a base.

The ketones of the formula (IV) required as starting substances in the preparation of the oxiranes of the formula (II) can be prepared by processes which are known in principle (compare, for example, the preparation examples).

The dimethyloxosulphonium methylide of the formula (V) required in process variant (α) is known (compare J. Amer.Chem.Soc. 87, 1363–1364 (1965)). In the above reaction, it is processed in the freshly prepared state, by being produced in situ by reaction of trimethyloxosulphonium iodide with sodium hydride, sodium amide or potassium tert.-butylate in the presence of a diluent.

The trimethylsulphonium methyl-sulphate of the formula (VI) required in process variant (β) is likewise known (compare Heterocycles 8, 397 (1977)). In the above reaction, it is likewise used in the freshly prepared state, by being produced in situ by reaction of dimethyl sulphide with dimethyl sulphate.

Dimethyl sulphoxide is preferably used as the diluent in variant (α) of the process for the preparation of the oxiranes of the formula (II).

The reaction temperatures can be varied within a substantial range in process variant (α) described above. In general, the reaction is carried out at temperatures between 20° C. and 80° C.

The process for the preparation of the oxiranes of the formula (II) by variant (α) and the working up of the reaction mixture obtained in this synthesis are carried out by customary methods (compare J.Amer.Chem.Soc. 87, 1363–1364 (1965)).

Acetonitrile is preferably used as the inert organic solvent in variant (β) of the preparation of the oxiranes of the formula (II).

Strong inorganic or organic bases can be used as the base in process variant (β). Sodium methylate is preferably used.

The reaction temperatures can be varied within a certain range in process variant (β) described above. In general, the reaction is carried out at temperatures between 0° C. and 60° C., preferably at room temperature.

The process for the preparation of the oxiranes of the formula (II) by variant (β) and the working up of the reaction product obtained in this synthesis are carried out by customary methods (compare Heterocycles 8, 397 (1977)).

If appropriate, the oxiranes of the formula (II) can be further reacted directly in the process according to the invention, without being isolated.

Formula (III) provides a general definition of the 1,2,4-triazoles also to be used as starting substances for the process according to the invention. In this formula, M preferably represents hydrogen, sodium or potassium.

The 1,2,4-triazoles of the formula (III) are generally known compounds of organic chemistry.

Possible diluents for the process according to the invention are organic solvents which are inert under the reaction conditions. These include, preferably, alcohols, such as, for example, ethanol, methoxyethanol or propanol; ketones, such as, for example, 2-butanol; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Possible bases for the reaction according to the invention are all the inorganic and organic bases which can customarily be used. These include, preferably, alkali metal carbonates, such as, for example, sodium carbonate and potassium carbonate; alkali metal hydroxides, such as, for example, sodium hydroxide; alkali metal alcoholates, such as, for example, sodium methylate and ethylate and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out the process according to the invention. In general, the reaction is carried out at temperatures between 0° C. and 200° C., preferably between 60° C. and 150° C.

In carrying out the process according to the invention, 1 to 2 mols of 1,2,4-triazole and, if appropriate, catalytic to 2-molar amounts of base are preferably employed per mol of oxirane of the formula (II). The end products are isolated in the generally customary manner.

The compounds of the formula (I) obtainable by the process according to the invention can be converted into acid addition salts or metal salt complexes.

The following acids can preferably be used for the preparation of physiologically acceptable acid addition salts of the compounds of the formula (I): the hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which, preferably, are derived from the following acids: hydrogen halide acids, such as, for example, hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compounds of the formula (I). The metal salt complexes can be isolated in a known manner, for example by filtration, and if appropriate purified by recrystal- lization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating rice diseases, such as *Pyricularia oryzae* and *Pellicularia sasakii*, cereal diseases, such as *Leptosphaeria nodorum, Puccinia recondita,* powdery mildew, *Cochliobolus sativus* and *Pyrenophora teres,* and vegetable and fruit diseases, such as *Sphaerotheca fuliginea* and *Venturia inaequalis.*

It should be emphasised that the substances according to the invention not only have a protective action but in some cases also have a systemic action. Thus, it is possible to protect plants from fungal attack if the active compound is fed to the above-ground parts of the plant via the soil and the root or via the seed.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, oorn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs and azo-metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

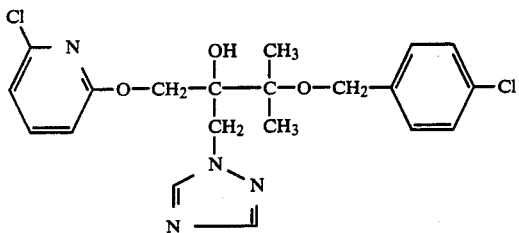

18.4 g (0.05 mol) of crude 2-[2-(4-chlorobenzyloxy)-prop-2-yl]-2-(6-chloropyridin-2-yloxymethyl)-oxirane are heated under reflux in 7 g (0.1 mol) of 1,2,4-triazole and 2 g of potassium carbonate in 100 ml of acetonitrile for a few hours (until all of the oxide has been consumed). The reaction mixture is then poured onto water and extracted with methylene chloride. The organic phase is dried over sodium sulphate and concentrated.

19 g (87% of theory) of 2-(4-chlorobenzyloxy)-3-(6-chloropyridin-2-yloxymethyl)-2-methyl-4-(1,2,4-triazol-1-yl)-3-butanol of refractive index $n_D^{20}=1.5618$ are obtained.

Preparation of the starting substance

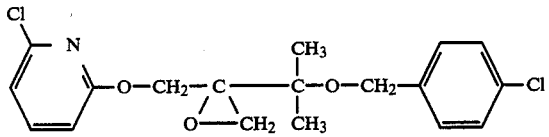

1.5 g (0.05 mol) of 80% pure sodium hydride are added in portions to a mixture of 11 g (0.05 mol) of trimethylsulphoxonium iodide and 60 ml of dimethylsulphoxide at 10° C., with stirring. The reaction mixture is stirred for 15 minutes, 17.7 g (0.05 mol) of 3-(4-chlorobenzyloxy)-(6-chloropyridin-2-yloxy)-3-methyl-2-butanone in a little dimethylsulphoxide are then added dropwise and the mixture is warmed at 60° C. for 1 hour. It is subsequently poured into water, under a nitrogen atmosphere, and extracted with methylene chloride. The organic phase is dried over sodium sulphate and concentrated. The crude 2-[2-(4-chlorobenzyloxy)-prop-2-yl]-2-(6-chloropyridin-2-yloxymethyl)-oxirane thus obtained is further reacted directly.

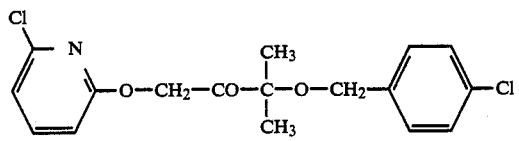

31 g (0.1 mol) of 1-bromo-3-(4-chlorobenzyloxy)-methyl-2-butanone in 200 ml of acetone are heated under reflux with 14 g (0.1 mol) of potassium carbonate and 13 g (0.1 mol) of 6-chloro-2-hydroxypyridine for 6 hours. Thereafter, the reaction mixture is poured into water and extracted with methylene chloride. The organic phase is dried over sodium sulphate and concentrated. 31.5 g (89% of theory) of 3-(4-chlorobenzyloxy)-1-(6-chloropyridin-2-yloxy)-3-methyl-2-butanone are obtained as a light-coloured oil.

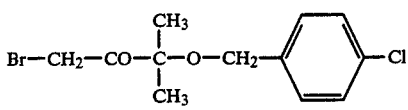

16.7 g (0.1 mol) of bromine are added dropwise to 22.7 g (0.1 mol) of 3-(4-chlorobenzyloxy)-3-methyl-2-butanone in 250 ml of methylene chloride at room temperature. After complete decolorization, the reaction mixture is poured into water. The organic phase is separated off, washed neutral with sodium bicarbonate solution and concentrated. The residue is distilled.

18 g (60% of theory) of 1-bromo-3-(4-chlorobenzyloxy)-3-methyl-2-butanone of boiling point 128° C. to 138° C. 0.03 mm Hg are obtained.

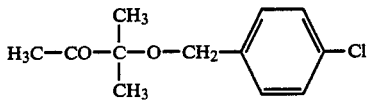

134 g (0.5 mol) of 2-(4-chlorobenzyloxy)-3,3-dimethoxy-2-methyl-butane are stirred in 1 liter of toluene with 100 g of ion exchanger (Levatit SP C118) and 200 ml of water at 60° C. for 8 hours. After the ion exchanger has been filtered off with suction, the organic phase is separated off, washed with water and concentrated in vacuo. The residue is distilled. 98 g (87% of theory) of 3-(4-chlorobenzyloxy)-3-methyl-2-butanone of boiling point 95° C. to 100° C./0.03 mm Hg are obtained.

The following compounds of the general formula (I) are obtained in an analogous manner corresponding to the process according to the invention:

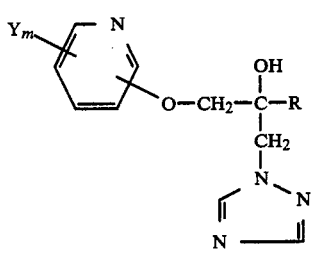

(I)

| Example No | R | Melting point (°C.) or $n_D^{20}$ |
|---|---|---|
| 2 | 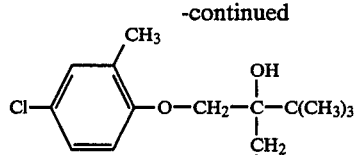 —C(CH₃)₂—S—C₆H₄—Cl (2-Cl-pyridyl) | 85–90 |
| 3 | (2-Cl-pyridyl)—C(CH₃)₂—O—C₆H₄—Cl | 72–75 |
| 4 | (2-Cl-pyridyl)—C(CH₃)₂—O—C₆H₄—C₆H₅ | 1.5848 |
| 5 | (3-pyridyl)—C(CH₂F)₂—CH₃ | 1.5088 |
| 6 | (2-Cl-pyridyl)—C₆H₄—Cl | 1.5523 |
| 7 | (2-Cl-pyridyl)—C₆H₄—C₆H₅ | 133 |

Use Examples

The substances shown below are used as comparison compounds in the use examples which follow:

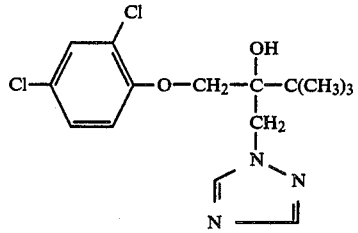 (A)

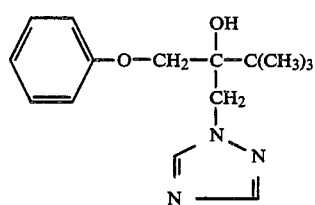 (B)

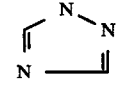 (C)

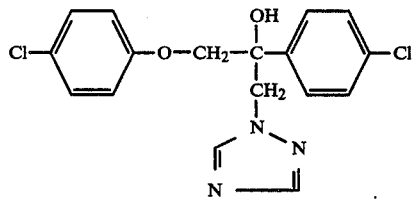 (D)

EXAMPLE A

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 7, 1 and 2.

EXAMPLE B

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 6, 7 and 3.

EXAMPLE C

Pellicularia test (rice)
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with *Pellicularia sasakii* and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to the following preparation examples: 6 and 7.

EXAMPLE D

Puccinia test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 7 and 1.

EXAMPLE E

Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compound according to the following preparation example: 6.

EXAMPLE F

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compound according to the following preparation example: 6.

EXAMPLE G

Venturia test (apple)/protective
Solvent: 4.7 parts by weight of acetone
Emulsifier: 0.3 parts by weight of alkylaryl polyglycol ether To produce a suitable preparation of compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compound according to the following preparation example: 6.

It will be understood that the specification and examples are illustrative but not limitative of the present invention and that other embodiments within the spirit and scope of the invention will suggest themselves to those skilled in the art.

We claim:
1. A triazolylmethyl-pyridyloxymethyl-carbinol of the formula

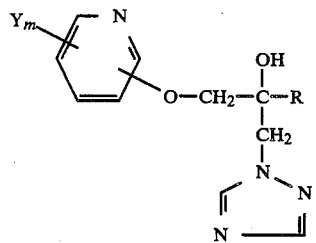

in which
R is a radical of the formula

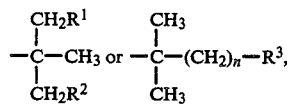

wherein
$R^1$ is hydrogen or halogen,
$R^2$ is halogen,
$R^3$ is $C_1$-$C_4$ alkoxy or $C_1$-$C_4$ alkylthio, halogenoalkoxy or halogenoalkylthio with in each case 1 or 2 carbon atoms and 1 to 5 identical or different halogen atoms; alkoxycarbonyl with 1 to 4 carbon atoms in the alkyl part; cyano; or phenoxy, phenylthio, phenylalkoxy with 1 to 4 carbon atoms in the alkyl part of phenylalkylthio with 1 to 4 carbon atoms in the alkyl part, each of which is unsubstituted or substituted on the phenyl by halogen or phenyl,
n is 0, 1 or 2,
Y is halogen, $C_1$-$C_4$ alkyl, $C_1$-$C_4$ alkoxy or cyano, and
m is 0, 1, 2, 3 or 4,
or an addition product thereof with an acid or metal salt.

2. A compound or addition product according to claim 1, wherein
$R^1$ is hydrogen, fluorine or chlorine,
$R^2$ is fluorine or chlorine
$R^3$ is methoxy, ethoxy; methylthio; ethylthio; trifluoromethoxy; trifluoromethylthio; methoxycarbonyl; ethoxycarbonyl; cyano; or phenoxy, phenylthio, phenylmethoxy or phenylmethylthio, each of which is unsubstituted or substituted by fluorine, chlorine phenyl,
n is 0, 1 or 2, and
Y is fluorine, chlorine, bromine, iodine, methyl, ethyl, methoxy or cyano.

3. A compound or addition product according to claim 1, wherein
$R^1$ is hydrogen, fluorine or chlorine,
$R^2$ is fluorine or chlorine,
$R^3$ is phenoxy, phenylthio, phenylmethoxy or phenylmethylthio, in each case unsubstituted or mono- or di-substituted by fluorine, chlorine or penyl,
Y is fluorine, chlorine, bromine or iodine, and
m is 0, 1, 2 or 3.

4. A 2-(4-chlorobenzyloxy)-3-(6-chloropyridin-2-yloxymethyl)-2- methyl-4-(1,2,4-triazol-1-yl)-3-butanol of the formula

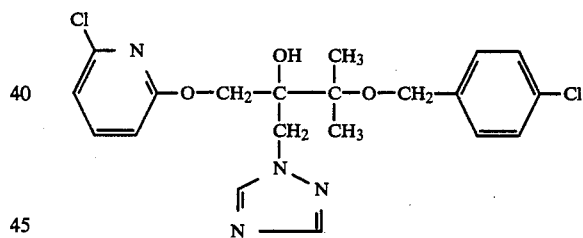

or an addition product thereof with an acid or metal salt.

5. A 2-(4-chlorophenylthio)-3-(6-chloropyridin-2-yloxymethyl)-2-methyl- 4-(1,2,4-triazol-1-yl)-3-butanol of the formula

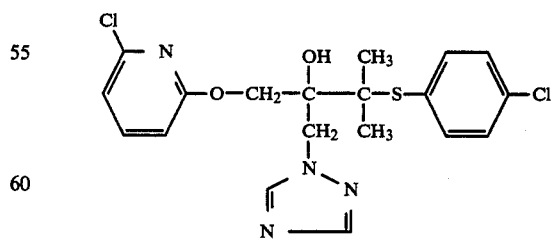

or an addition product thereof with an acid or metal salt.

6. A 2-(4-chlorophenoxy)-3-(6-chloropyridin-2-yloxymethyl)-2-methyl-4-(1,2,4-triazol-1-yl)-3-butanol of the formula

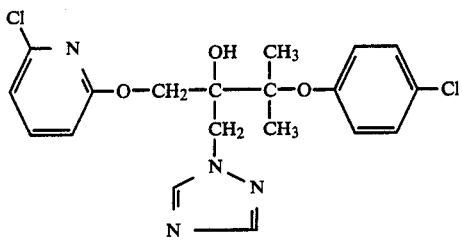

or an addition product thereof with an acid or metal salt.

7. A fungicidal composition comprising a fungicidally effective amount of a compound or addition product according to claim 1 in admixture with a diluent.

8. A method of combating fungi which comprises administering to such fungi or to a fungus habitat a fungicidally effective amount of a compound or addition product according to claim 1.

9. The method according to claim 8, wherein such compound is 2-(4-chlorobenzyloxy)-3-(6-chloropyridin-2-yloxymethyl)-2-methyl-4-(1,2,4-triazol-1-yl)-3-butanol, 2-(4-chlorophenylthio)-3-(6-chloropyridin-2-yloxymethyl)-2-methyl-4-(1,2,4-triazol-1-yl)-3-butanol, 2-(4-chlorophenyoxy-3-(6-chloropyridin-2-yloxymethyl)-2-methyl-4-(1,2,4-triazol-1-yl)-3-butanol, or an addition product thereof with an acid or metal salt.

* * * * *